US008710415B2

(12) United States Patent
Peyras

(10) Patent No.: US 8,710,415 B2
(45) Date of Patent: Apr. 29, 2014

(54) LIGHTING DEVICE WITH DEVICE FOR REGULATING THE ILLUMINATION ACCORDING TO THE LUMINANCE OF THE ILLUMINATION FIELD AND CORRESPONDING USE

(75) Inventor: Gabriel Peyras, Orleans (FR)

(73) Assignee: Maquet SAS, Ardon (FR)

( * ) Notice: Subject to any disclaimer, the term of this patent is extended or adjusted under 35 U.S.C. 154(b) by 809 days.

(21) Appl. No.: 12/885,037

(22) Filed: Sep. 17, 2010

(65) Prior Publication Data

US 2011/0068694 A1 Mar. 24, 2011

(30) Foreign Application Priority Data

Sep. 24, 2009 (FR) ..................................... 09 56604

(51) Int. Cl.
*G01J 1/32* (2006.01)
*A61B 1/06* (2006.01)

(52) U.S. Cl.
USPC .......................................... 250/205; 600/249

(58) Field of Classification Search
USPC .......................................... 250/205; 600/249
See application file for complete search history.

(56) References Cited

U.S. PATENT DOCUMENTS

| | | | | |
|---|---|---|---|---|
| 6,464,490 | B1 | 10/2002 | Chato | |
| 6,964,490 | B2 | 11/2005 | Scholz | |
| 2006/0152172 | A9 * | 7/2006 | Mueller et al. | 315/291 |
| 2009/0002982 | A1 | 1/2009 | Hu et al. | |

FOREIGN PATENT DOCUMENTS

| | | | | |
|---|---|---|---|---|
| EP | 0 544 559 | A1 | | 6/1993 |
| EP | 1 342 947 | A2 | | 9/2003 |
| EP | 1 568 937 | A1 | | 8/2005 |
| JP | 2007005191 | A | * | 1/2007 |

OTHER PUBLICATIONS

French Search Report for priority French application No. FR 0956604 mailed on May 31, 2010.
Written Opinion for priority French application No. FR 0956604.

* cited by examiner

*Primary Examiner* — Thanh Luu
(74) *Attorney, Agent, or Firm* — Merchant & Gould P.C.

(57) ABSTRACT

The device (1) for lighting an illumination field (2) includes a light source (5), adapted to illuminate the illumination field (2), a device for regulating the illuminance from the light source (7). The device for regulating the illuminance from the light source (7) is adapted to receive an actual luminance signal representing the actual luminance of the lighting field (2) and control the illuminance from the light source (5) as a function of the actual luminance signal and a luminance set point signal. The lighting device (1) comprises a device for determining the actual luminance (11) adapted to determine the actual luminance of the lighting field (2) and to create and transmit the actual luminance signal to the device for regulating the illumination from the light source (7). Application to devices for illuminating operating fields.

10 Claims, 4 Drawing Sheets

LIGHTING DEVICE WITH DEVICE FOR REGULATING THE ILLUMINATION ACCORDING TO THE LUMINANCE OF THE ILLUMINATION FIELD AND CORRESPONDING USE

This application claims benefit of Serial No. 09 56604, filed Sep. 24, 2010 in France and which application is incorporated herein by reference. A claim of priority to all, to the extent appropriate is made.

The present invention concerns a device for lighting an illumination field, in particular an operating area, including

- a light source, adapted to light the illumination field; and
- a device for regulating the illuminance from the light source.

Operating lights provide a large quantity of light (40,000 lux to 160,000 lux) in the operating field and thus allow the surgeon to work under good conditions.

This large quantity of light is necessary due to the low reflectivity of certain human tissues, such as muscles and certain tissues of the digestive system, and because the human eye has a better resolution for high luminance.

However, excessively strong luminance can also overwhelm, fatigue and degrade the viewer's vision.

During a same operation, the surgeon must observe different types of tissue with different reflectivity depending on the tissue. Skin, bones, certain parts of the colon, are very reflective and lead, for a given illuminance high luminances perceived by the surgeon's eye. Other tissue is very dark and produces low luminance for a given illuminance. The surface shape of the observed tissues also evolves during the operation, and can lead to variations in the illumination received by the tissue, and as a result, to a variation in the illuminance of these tissues perceived by the surgeon. Thus, when the surgeon cuts at the operation site, a cavity forms in which the illuminance is lower. The tissues then retransmit a lower luminance toward the surgeon's eye than that of the location before the operation, independently of the reflectivity of the tissue. The luminance is therefore made up of two elements: the "luminance factor," depending solely on the reflectivity of the surface, and the "luminance coefficient," depending solely on the surface shape.

The known operating lighting devices are equipped with a system for adjusting the illuminance that requires a manual intervention by the user and makes it possible to modify the luminance flux of the lighting device when the type of tissue observed changes.

U.S. Pat. No. 6,964,490, for example, concerns a device for lighting an operating field adapted to adjust the luminance flux depending on the size of the lighting field to keep the illuminance at an essentially constant level. The means detecting the change in the size of the lighting field can be, among others, an optical detector adapted to detect the variation of the luminance of the operating field. The detected luminance variation is then used to adjust the illuminance to a predetermined level, by changing the luminance flux.

These operating lighting devices are not adapted to modify the illuminance level as a function of the luminance, i.e. as a function of the luminance factor depending solely on the reflectivity of the observed tissues and/or the luminance coefficient depending solely on the surface shape of the lighted area, and therefore do not make it possible to maintain or obtain ideal luminance for the surgeon's comfort, in particular when the tissue or shape of the operating field changes.

The present invention aims to offset this drawback and to propose a lighting device adapted to create better lighting of the lighting field, preferably without human intervention. To that end, the object of the invention is a device of the aforementioned type, characterized in that the device for regulating the illuminance from the light source is adapted to (a) receive an actual luminance signal representing the actual luminance of the lighting field; and (b) control the illuminance from the light source as a function of the actual luminance signal and a luminance set point signal, and the lighting device comprises a device for determining the actual luminance adapted to determine the actual luminance of the lighting field and to create and transmit the actual luminance signal to the device for regulating the illuminance from the light source.

According to other embodiments, the invention includes one or several of the following features:

It also comprises a human-machine interface adapted to capture luminance set point information and generate the luminance set point signal of the lighting field.

It also comprises a device for adjusting the illuminance from the light source, controlled by the device for regulating the illuminance from the light source.

The device for adjusting the illuminance from the light source is adapted to vary the illuminance from the light source by one of the following features:

- variation of the luminance flux from the light source; and
- variation of the opening of an orifice arranged between the light source and the lighting field;
- movement of an optical piece, such as the rotation of a polarizer in relation to a second polarizer such that the angle between their axes, and thus the outgoing luminous flux, is controlled, the two polarizers being placed between the light source and the lighting field.

The device for regulating the illuminance from the light source is adapted to:

- compare a difference between the actual luminance signal and the luminance set point signal to a limit luminance deviation value
- control the device for adjusting the illuminance from the light source when the difference is greater than the limit luminance deviation value to cause the illuminance from the light source to vary such that the difference becomes less than or equal to the limit luminance deviation value, and preferably becomes equal to 0.

when the absolute value of the difference is smaller than the limit luminance deviation value, the device for regulating the illuminance from the light source does not control the device for adjusting the illuminance from the light source or controls it for maintenance of the illuminance;

The device for regulating the illuminance from the light source is adapted to periodically receive the actual luminance signal through the device for determining the actual luminance and the luminance set point signal.

The device for determining the actual luminance comprises:

- at least one photodiode arranged on a support, or
- at least one CCD camera arranged on a support.

The device for determining the actual luminance comprises two modules for determining the actual luminance and means adapted to detect an obstacle situated between one of the modules for determining the actual luminance and the lighting field; and the actual luminance signal transmitted to the device for regulating the illuminance from the light source is that associated with the other module for determining the actual luminance.

Said device for regulating the lighting from the light source comprises a processor and a memory.

The invention also concerns a use of a device as mentioned above to light a physician's operating area.

The invention will be better understood upon reading the description that follows, provided solely as an example and done in reference to the appended drawings, in which.

Figure 4:
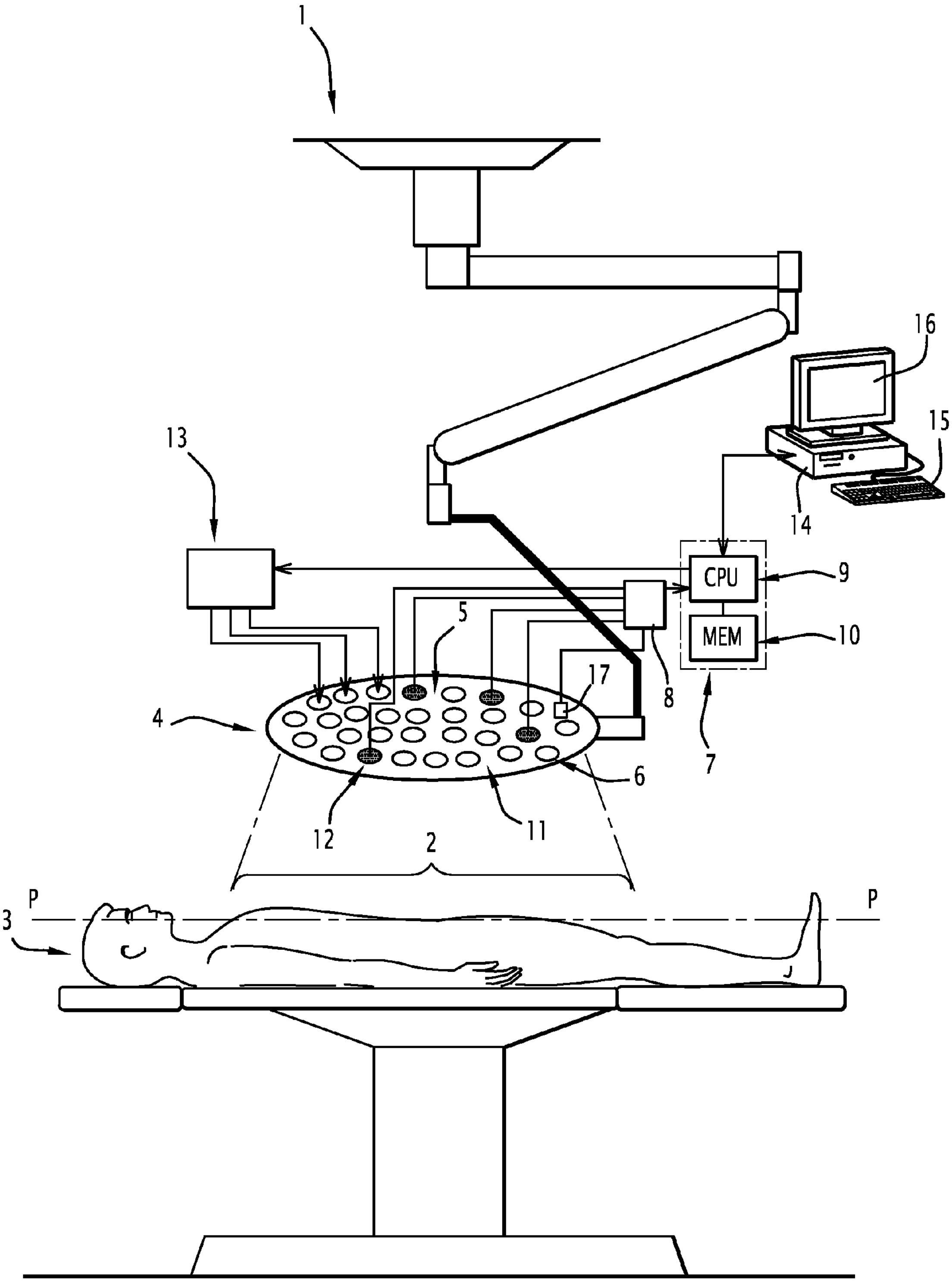
FIG. 4 is a diagrammatic view of a lighting installation including a lighting device according to the invention.

FIG. 4 shows a lighting device according to the invention, designated by reference 1. The lighting device 1 is intended to illuminate a lighting field 2 extending along a lighting plane P-P, in particular horizontal. In this case, the lighting field 2 is a physician's operating field on a patient 3 in a medical operating room.

The lighting device 1 comprises a support 4 on which a light source 5 is arranged made up of a plurality of lighting elements 6 and adapted to illuminate the lighting field 2. The lighting device 1 also comprises a device 7 for regulating the illuminance from the light source 5. This device 7 for regulating the illuminance from the light source comprises an inlet filter 8, a processor 9 and a memory 10.

The lighting device 1 also comprises a device for determining the actual luminance 11 adapted to determine the actual luminance of the lighting field 2.

This device for determining the actual luminance 11 is provided with a plurality of modules for determining the actual luminance 12 distributed on the support 4, in particular photodiodes and/or a CCD camera, or any other system adapted to that end. In the event the device for determining the actual luminance 11 comprises a plurality of photodiodes, each photodiode is provided with an optical system combining the lighting field 2 and the photodiode. When the device for determining the actual luminance 11 comprises a CCD camera, the CCD camera captures the lighting field 2 and has an output determining the actual luminance from pixel gray levels, from the exposure time calculated by the automatic adjustment system of the exposure time or the opening diameter calculated by the automatic adjustment system for the opening diameter.

The lighting device 1 also comprises a device for adjusting the illuminance 13 of the light source and a human-machine interface 14. The human-machine interface 14 comprises an entry means 15 adapted to capture set point values and a visualization means 16 adapted to visualize the values entered and the state of the lighting device 1. The set point values are in particular set point values for the luminance of the lighting field 2 without being limited thereto.

The lighting device 1 also comprises means for detecting obstacles 17 arranged on the support 4 and adapted to detect obstacles, such as arms, for instance, situated between one of the modules for determining the actual luminance 12 and the lighting field 2 and adapted to communicate with the input filter 8 of the device 7 for regulating the illuminance from the light source.

Figure 5:
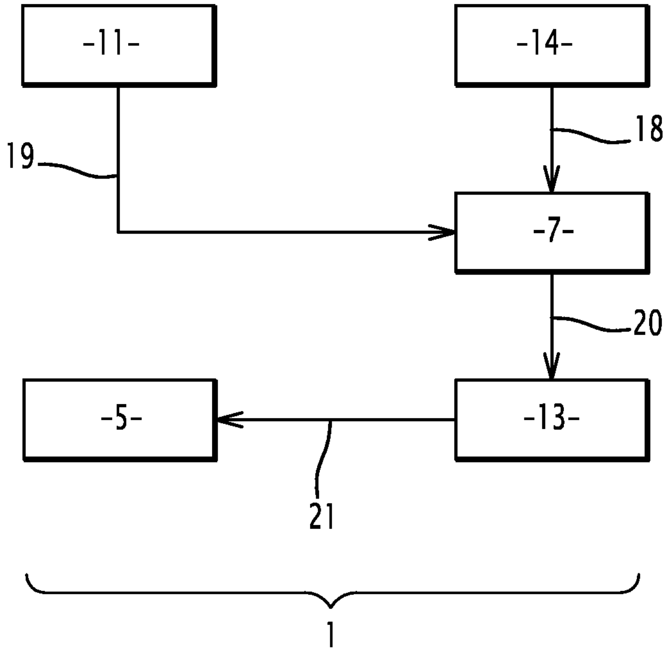
FIG. 5 is a diagrammatic illustration of the functional modules of the lighting device according to the invention.

FIG. 5 shows the functional modules of the lighting device 1 according to the invention. Each of the functional blocks corresponds to one of the structural elements described above in reference to FIG. 4. The different modules of the lighting device 1, i.e. the light source 5, the device for regulating the illuminance from the light source 7, the device for determining the actual luminance 11, the device for adjusting the illuminance from the light source 13, the human-machine interface 14 and the means adapted to detect obstacles 17, are coupled to each other by connections, illustrated by arrows, 18 to 21 in FIG. 5, the direction of arrows 18 to 21 indicating the direction of transmission of information or the direction of transmission of a command between the respective elements.

The device operates as follows.

The user of the lighting device 1 enters, via the human-machine interface 14, a luminance set point value corresponding to the desired luminance. The set point value therefore represents a determined luminance of the lighting field. Preferably, the luminance set point value is entered at the beginning of use, but it is also possible to enter it or change it during use of the lighting device 1. This luminance set point value is transmitted via a connection 18 to the device 7 for regulating the illuminance from the light source and is stored in the memory 10. The device 11 for determining the actual luminance determines the actual luminance of the lighting field 2 and creates an actual luminance signal of the lighting field 2 that is transmitted via the connection 19 to the input filter 8 of the device 7 for regulating the illuminance from the light source and that is then stored in the memory 10. The processor 9 of the device for regulating the illuminance from the light source 7 determines the difference between the actual luminance value and the luminance set point value, as well as the absolute value of that difference, and compares said absolute value of the difference to a limit luminance deviation value.

If the absolute value between the actual luminance value and the luminance set point value is less than or equal to the limit luminance deviation value, the device for regulating the illuminance from the light source 7 does not control the device 13 for adjusting the illuminance from the light source or controls it to maintain the illuminance. Then, the regulating device 7 again reads an actual luminance value received by the device for determining the actual luminance 11 and repeats the described process.

If the absolute value of the difference between the actual luminance value and the luminance set point value is greater than the limit luminance deviation value, the device 7 for regulating the illuminance from the light source controls the device 13 for adjusting the illuminance of the light source in a direction tending to decrease the deviation between the actual luminance value and the luminance set point value. Then, the device 13 for adjusting the illuminance from the light source acts on the light source 5 to increase or decrease the illuminance from the light source 5 as a function of the command. More precisely, the device for adjusting the illuminance from the light source 13 causes the illuminance from the light source 5 to vary. Preferably, this variation is done by varying the luminous flux of the light source 5 without modifying the size of the lighting field 2.

The illuminance from the light source is defined as the luminous flux from the light source 5 received by a surface unit.

After adjusting the illuminance from the light source 5, the luminance of the lighting field 2 is once again determined by the device 11 for determining the actual luminance and the procedure described above is repeated as many times as needed until the absolute value of the difference between the actual luminance value and the luminance set point value becomes less than or equal to the limit luminance deviation value, and preferably becomes equal to 0.

When the detection means 17 detects an arm or another obstacle between the lighting field 2 and one of the modules for determining the actual luminance 12, a corresponding signal is transmitted to the input filter 8 of the device for regulating the illuminance from the light source 7 and the respective luminance value determined by the module for determining the actual luminance 12 is blocked by the input filter 8, and the illuminance is therefore regulated as a function of all of the luminance values determined by the other modules for determining the actual luminance 12.

The device for determining the actual luminance 11 determines the actual luminance of the lighting field 2 periodically or continuously and the device for regulating the illuminance from the light source 7 periodically receives an actual luminance value from the device for determining the actual luminance 11. The length of the period is chosen such that the illuminance from the light source 5 can be modified dynamically without the lighting device 1 user's eye being exposed to a lighting field 2 with a luminance essentially different from the luminance set point value last entered and currently in force.

When the actual luminance differs from the set point by a value greater than the limit deviation, the lighting device 1 is adapted to bring the actual luminance to the limit deviation value, in a time that does not exceed 2000 ms, and more advantageously not 500 ms.

To vary the illuminance from the light source 5, different parameters of the lighting device 1 can be varied by the device for adjusting the illuminance from the light source 13. The modifications include:

- varying the luminous flux of the light source 5, for example, by the intensity of power from the light source 5,
- varying the opening of an orifice arranged between the light source 5 and the lighting field 2,
- moving an optical piece, such as the rotation of a polarizer in relation to a second polarizer, so that the angle between their axes, and thus the outgoing luminous flux, is controlled, the two polarizers being placed between the light source 5 and the lighting field 2.

The lighting device 1 therefore modifies the illuminance as a function of the actual luminance of the lighting field 2, determined by the device for determining the actual luminance 11, and as a function of the luminance set point value determined by the user via the human-machine interface 14. The modification of the illuminance occurs autonomously. The term "autonomous" means that the lighting device 1 is adapted to modify the illuminance without requiring human intervention during that modification.

Figure 1:
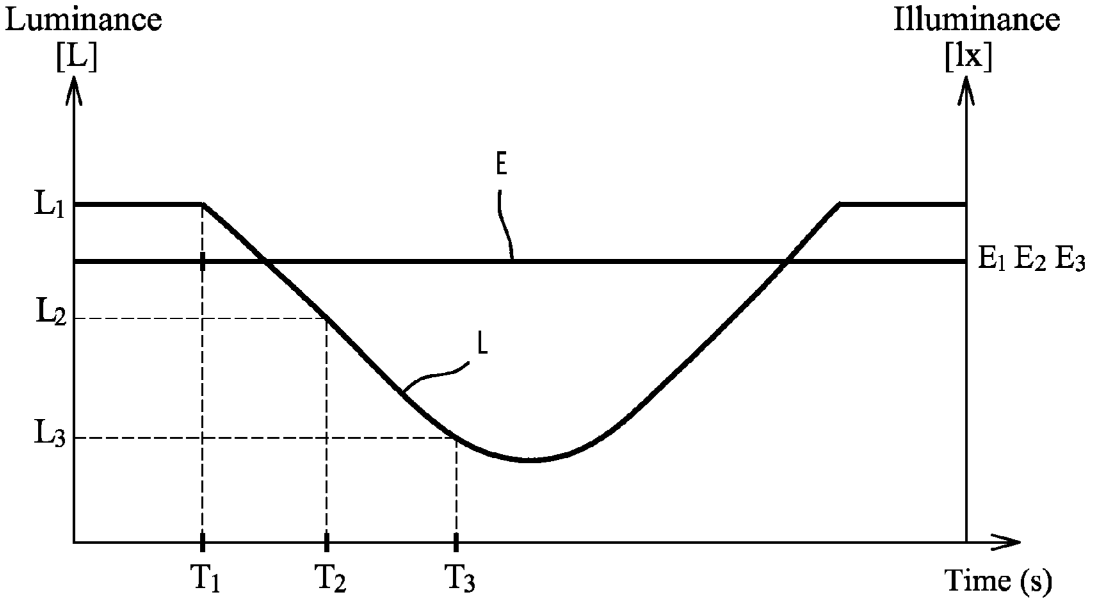
FIG. 1 is a diagram illustrating the appearance of the luminance of a lighting field during an operation with constant illuminance according to the state of the art.

FIG. 1 shows a diagram of an example of luminance variation of a lighting field with constant illuminance during a surgical operation with a lighting device according to the state of the art. The x-axis shows the time T, the left axis indicates the luminance of the lighting field. The appearance of the luminance over time is referenced L. The right axis indicates the illuminance and the aspect of the illuminance is referenced E. One notes that the luminance at moment $T_1$, corresponding to the beginning of the operation (assuming for example that the operation in question is not an operation in a cavity of the gynecological, oral, etc. . . . type), is high for a given illuminance $E_1$. This is due to the fact that the superficial tissues are relatively reflective, which implies that a large portion of the light emitted by the lighting device is returned. During the operation, the surgeon is called on to intervene progressively deeper in the tissues and a cavity therefore forms. During times $T_2$ and $T_3$, there is therefore a decrease in the luminance due to a significant absorption of the light by these tissues and/or due to a location in a cavity. Once the surgeons' operation is done, he sutures the wound, which translates to a new increase in the constant illuminance luminance E1. FIG. 1 also shows the evolution of the illuminance emitted by the light source. One therefore sees that no stress changing the illuminance took place, which translates to a constant level of illuminance from the light source.

Figure 2:
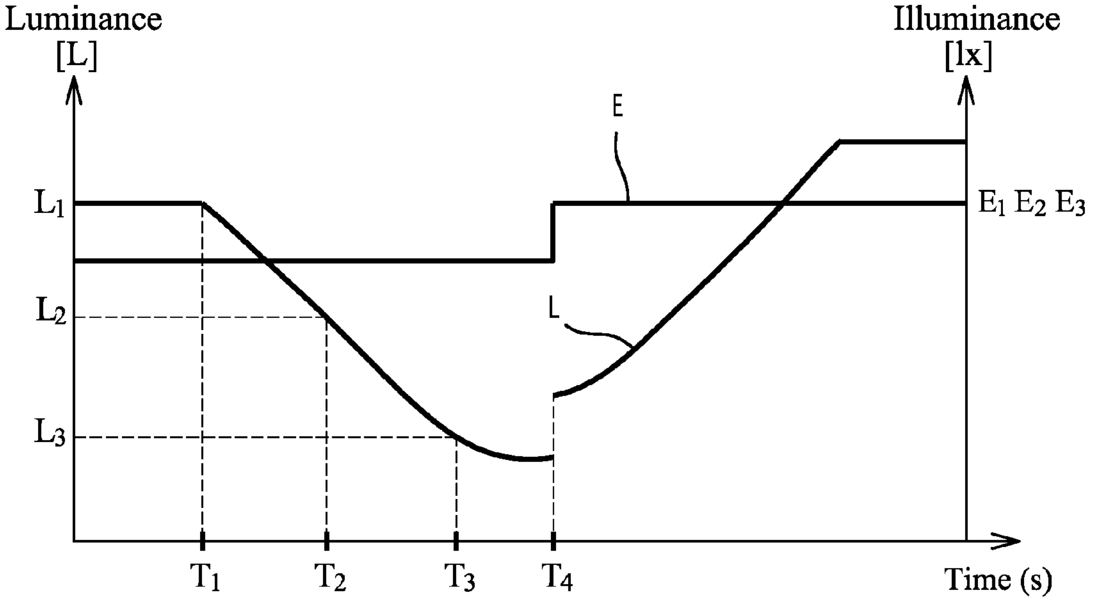
FIG. 2 is a diagram illustrating the appearance of the luminance of a lighting field during a non-constant illuminance operation according to the state of the art.

FIG. 2 indicates the same situation as that described above in reference to FIG. 1, but at a moment $T_4$ an increase in the illuminance from the light source occurs through user intervention. This leads, in the lighting devices of the prior art, to a jump in the actual luminance, on the condition that at the moment $T_4$ the other parameters remain unchanged.

Figure 3:
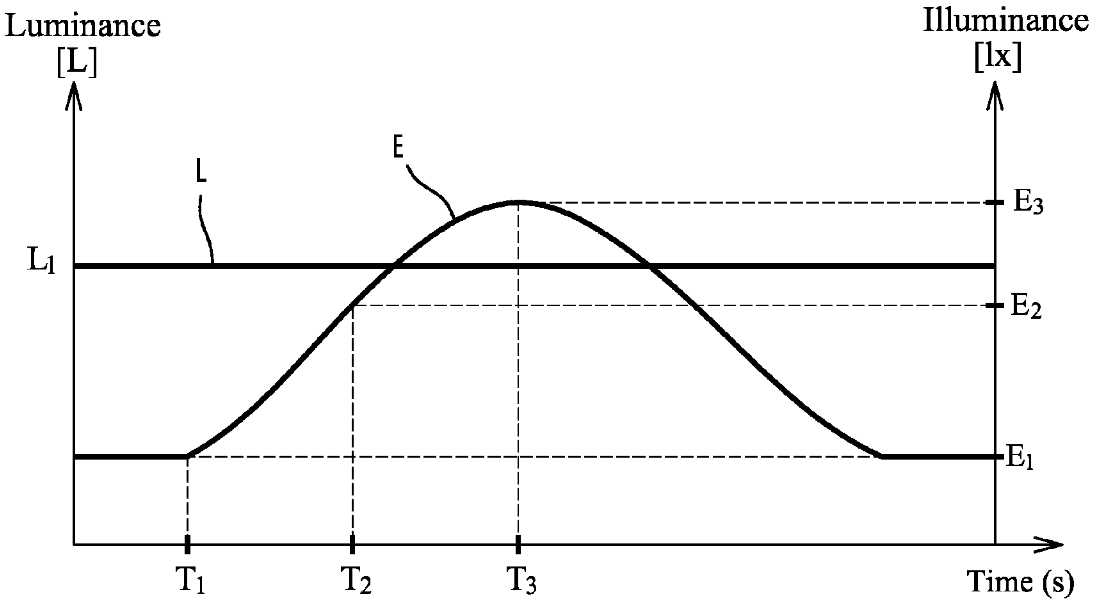
FIG. 3 is a diagram illustrating the modification of the illuminance to keep the luminance of the lighting field constant during an operation according to the invention.

FIG. 3 shows a diagram of the type of the diagrams of FIGS. 1 and 2 showing the appearance of the luminance and of the illuminance during an operation with a lighting device 1 according to the invention, which is adapted to keep the actual luminance during the time at a constant level where, within a limit deviation, even in the presence of changes in tissue reflectivity and/or surface and cavity locations. The advantage of this lighting device 1 is visual comfort for the user as well as the absence of a need for that same user to modify the illuminance set point when the reflectivity and/or surface shape change. The illuminance from the light source 5 is modified and adjusted automatically as a function of the actual luminance of the lighting field 2. When one of the reflectivity/luminance factor and/or surface shape/luminance coefficient of the lighting field 2 changes so as to create an increase in the luminance, the illumination is adjusted to a lower level to avoid an excessively high actual luminance level. Conversely, when one of the reflectivity/luminance factor and/or surface shape/luminance coefficient of the lighting field 2 changes so as to create a decrease in the luminance, the device for regulating the illuminance from the light source 7 increases the illuminance to avoid a loss of luminance due to the absorption of the light by the tissues or by the surface shape of the lighting field 2.

The information transmitted between the different components described above is transmitted through values. However, in particular in the case of analog systems, the information can be transmitted by signals other than values, for example electrical voltages or frequencies.

The lighting device 1 according to the invention is in particular intended for operating lighting for surgery, but can also be applied to the dental field.

The lighting device 1 comprises a device for determining the actual luminance 11 adapted to determine the actual luminance of the lighting field 2 and to create and transmit the actual luminance signal to the device 7 for regulating the illuminance from the light source as a function of the reflectivity of the lighting field 2. The lighting device 1 is also adapted to bring or keep the luminosity of the lighting field 2 within a luminosity set point range or to a luminosity set point when the reflectivity of the lighting field 2 changes.

The lighting device therefore has the following features. It is an operating lighting device comprising means for estimating the actual luminance of the lighting field or of the lit object, in particular as a function of the reflectivity and surface shape of the object or lighting field, and means for regulating the illuminance by the operating light to a luminance value determined as a function of the estimated luminance.

The determined luminance value is preferably constant over a determined period, in particular over at least 1 min.

| French | English |
|---|---|
| Luminance | Luminance |
| Eclairement | Illumination |
| Temps (s) | Time (s) |

The invention claimed is:

1. A device for lighting an illumination field, in particular an operating field, of the type including a light source, adapted to light the illumination field a device for regulating the illuminance from the light source wherein the device for regulating the illuminance from the light source is adapted to (a) receive an actual luminance signal representing the actual luminance of the lighting field and (b) control the illuminance from the light source as a function of the actual luminance signal and a luminance set point signal, and in that the lighting device comprises a device for determining the actual luminance of the lighting field and to create and transmit the actual luminance signal to the device for regulating the illuminance from the light source, said device for determining the actual luminance comprising two modules for determining the actual luminance and means adapted to detect an obstacle situated between one of the modules for determining the actual luminance and the lighting field, wherein the actual luminance signal transmitted to the device for regulating the illuminance from the light source is that associated with the other module for determining the actual luminance.

2. The lighting device according to claim 1, wherein it also comprises a human-machine interface that is adapted to capture luminance set point information and generate the luminance set point signal for the lighting field.

3. The lighting device according to claim 1, wherein it also comprises a device for adjusting the illuminance from the light source, controlled by the device for regulating the illuminance from the light source.

4. The lighting device according to claim 3, wherein the device for adjusting the illuminance from the light source is adapted to vary the illuminance from the light source by one of the following features:

varying the luminous flux of the light source, varying the opening of an orifice arranged between the light source and the lighting field, moving an optical piece, such as the rotation of a polarizer in relation to a second polarizer, so that the angle between their axes, and thus the outgoing luminous flux, is controlled, the two polarizers being placed between the light source and the lighting field.

5. The lighting device according to claim 3, wherein the device for regulating the illuminance from the light source is adapted to compare a difference between the actual luminance signal and the luminance set point signal to a limit luminance deviation value control the device for adjusting the light source when the difference is greater than the limit luminance deviation value to cause the illuminance from the light source to vary such that the difference becomes less than or equal to the limit luminance deviation value, and preferably becomes equal to 0.

6. The lighting device according to claim 5, wherein when the absolute value of the difference is less than the limit luminance deviation value, the device for regulating the illuminance from the light source does not control the device for adjusting the illuminance from the light source or controls it to maintain the illuminance.

7. The lighting device according to claim 1, wherein the device for regulating the illuminance from the light source is adapted to periodically receive the actual luminance signal by the device for determining the actual luminance and the luminance set point signal.

8. The lighting device according to claim 1, wherein the device for determining the actual luminance comprises at least one photodiode arranged on a support, or at least one CCD camera arranged on a support.

9. The lighting device according to claim 1, wherein said device for regulating the illuminance from the light source comprises a processor and a memory.

10. A use of a lighting device according to claim 1 to light a physician's operating field.

* * * * *